United States Patent [19]
Cohen et al.

[11] Patent Number: 5,135,485
[45] Date of Patent: Aug. 4, 1992

[54] CAPACITANCE-TYPE FLUID LEVEL SENSOR FOR I.V. AND CATHETER BAGS

[76] Inventors: Louis Cohen, 400 E. Randolph, Apt. 2603, Chicago, Ill. 60601; Richard A. Rose, 895 Dexter La., Hoffman Estates, Ill. 60194

[21] Appl. No.: 660,661

[22] Filed: Feb. 25, 1991

[51] Int. Cl.⁵ .............................................. A61M 31/00
[52] U.S. Cl. ...................................... 604/67; 604/31; 604/65; 324/606
[58] Field of Search ................................ 604/27–31, 604/50, 65, 66, 67, 4, 123, 131, 151, 153, 207, 260; 128/DIG. 12, DIG. 13; 324/606

[56] References Cited

U.S. PATENT DOCUMENTS

| | | | |
|---|---|---|---|
| 2,772,394 | 11/1956 | Bradley | 324/61 |
| 2,885,633 | 5/1959 | Cook | 324/1 |
| 2,934,699 | 4/1960 | Offner | 324/57 |
| 3,043,993 | 7/1962 | Maltby | 317/146 |
| 3,086,109 | 4/1963 | Kaehms | 246/249 |
| 3,136,952 | 6/1964 | Hamby et al. | 328/140 |
| 3,375,716 | 4/1968 | Hersch | 73/304 |
| 3,543,046 | 11/1970 | Tiffany | 307/118 |
| 3,566,259 | 2/1971 | Wilson | 324/61 |
| 3,612,997 | 11/1971 | Paulkovich | 324/60 |
| 3,646,541 | 2/1972 | Rathbun | 340/244 |
| 3,694,742 | 9/1972 | Bergmanis et al. | 324/61 |
| 3,747,407 | 7/1973 | Wallman | 73/304 |
| 3,805,156 | 4/1974 | Norton et al. | 324/61 |
| 3,883,800 | 5/1975 | Dupont | 324/61 |
| 4,016,490 | 4/1977 | Weckenmann et al. | 324/61 |
| 4,099,118 | 7/1978 | Franklin et al. | 324/61 |
| 4,145,619 | 3/1979 | Tseng | 307/118 |
| 4,146,834 | 3/1979 | Maltby et al. | 324/60 |
| 4,347,740 | 7/1982 | Townsend | 73/304 |
| 4,642,555 | 2/1987 | Swartz et al. | 324/60 |
| 4,820,268 | 4/1989 | Kawamura et al. | 604/67 |
| 4,890,491 | 1/1990 | Vetter et al. | 73/290 |
| 4,898,578 | 2/1990 | Rubalcaba, Jr. | 604/66 |
| 4,976,687 | 12/1990 | Martin | 604/65 |
| 4,995,268 | 2/1991 | Ash et al. | 604/67 X |
| 5,006,997 | 4/1991 | Reich | 604/27 X |
| 5,078,682 | 1/1992 | Miki et al. | 604/65 |

OTHER PUBLICATIONS

Marsh, J. K., "Two Frequency Oscillator Detects Level of Liquid", *Electronics*, Mar. 20, 1967, p. 90.

*Primary Examiner*—John D. Yasko
*Attorney, Agent, or Firm*—Welsh & Katz, Ltd.

[57] ABSTRACT

A capacitance-type fluid level sensing system, method, and device is disclosed for determining the amount of fluid in a container, for example, a disposable plastic bag used for intravenous (i.v.) injection or collection of waste from a human body (catheter). In one illustrated embodiment, conductive plates are disposed on the outside of the plastic bag and connected to a circuit for detecting any change in the capacitance of the capacitor formed thereby. In another embodiment, the conductive plates are integrally constructed as part of a surface of the electronic device housing, such that the fluid level can be detected when the housing is affixed directly to the outside of the bag. Alternative annunciation, detection, flow rate calculation, display, and housing features are shown in various embodiments.

43 Claims, 7 Drawing Sheets

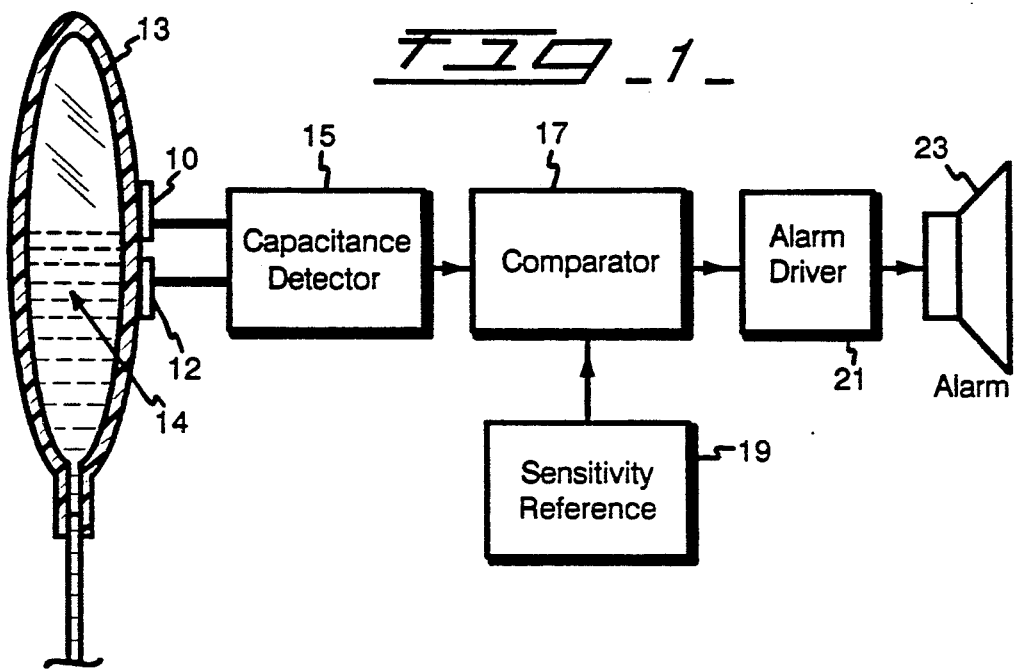
FIG_1_
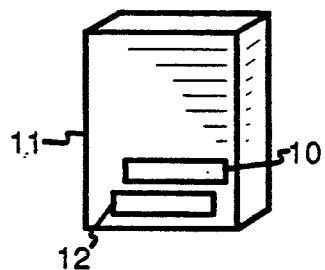
FIG_2_
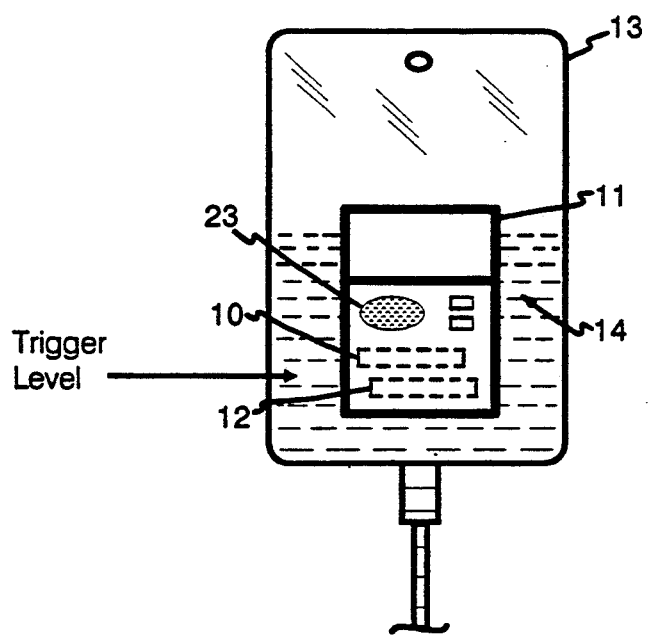
FIG_3_

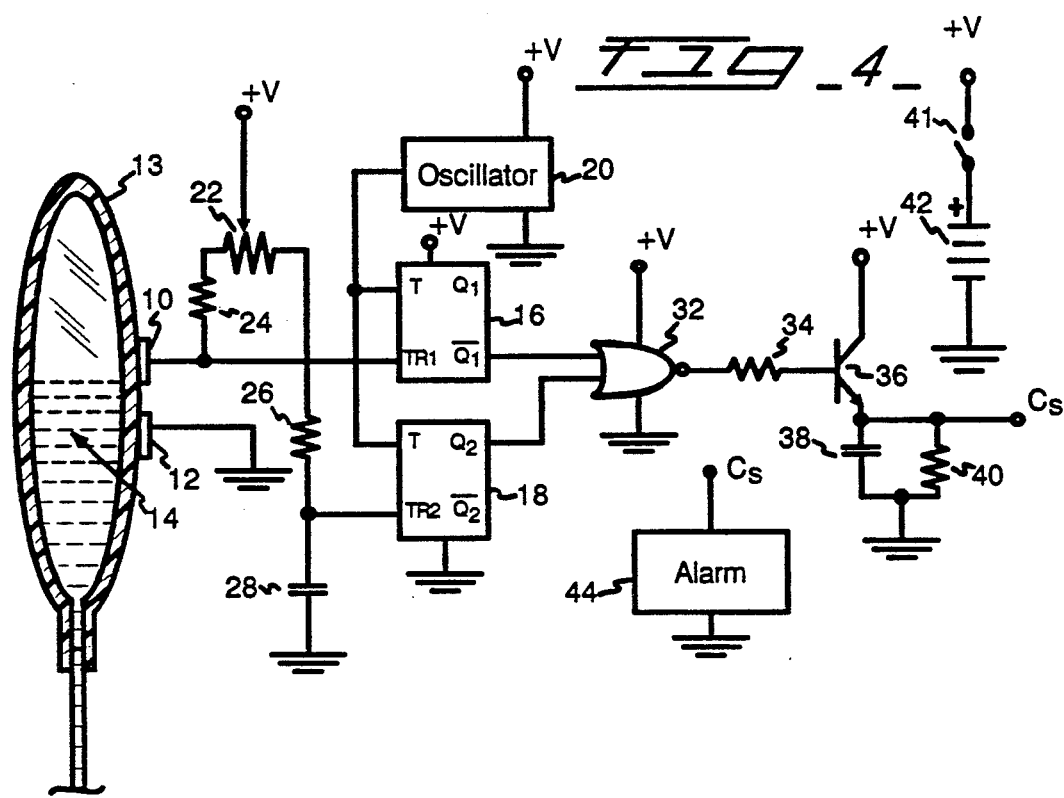
FIG_4_
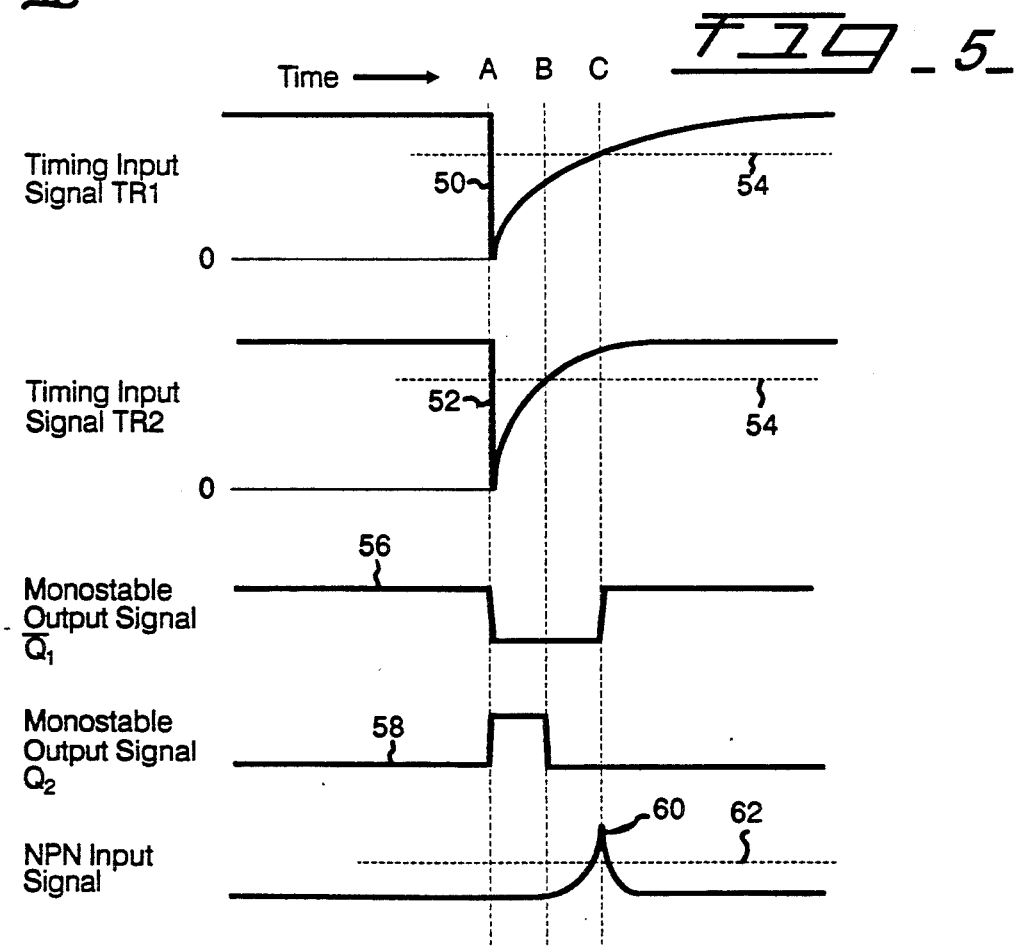
FIG_5_

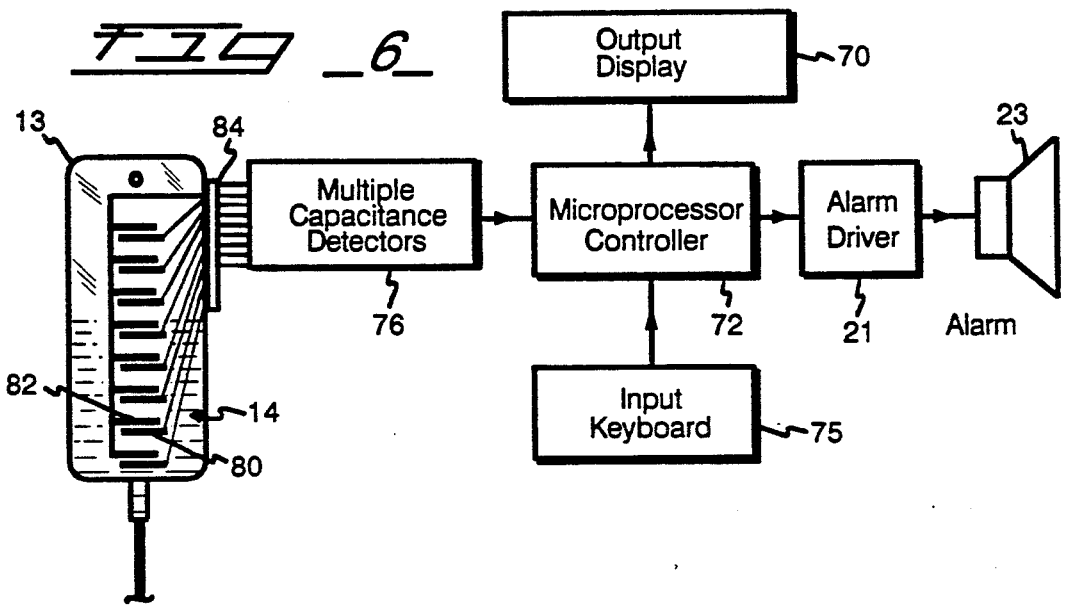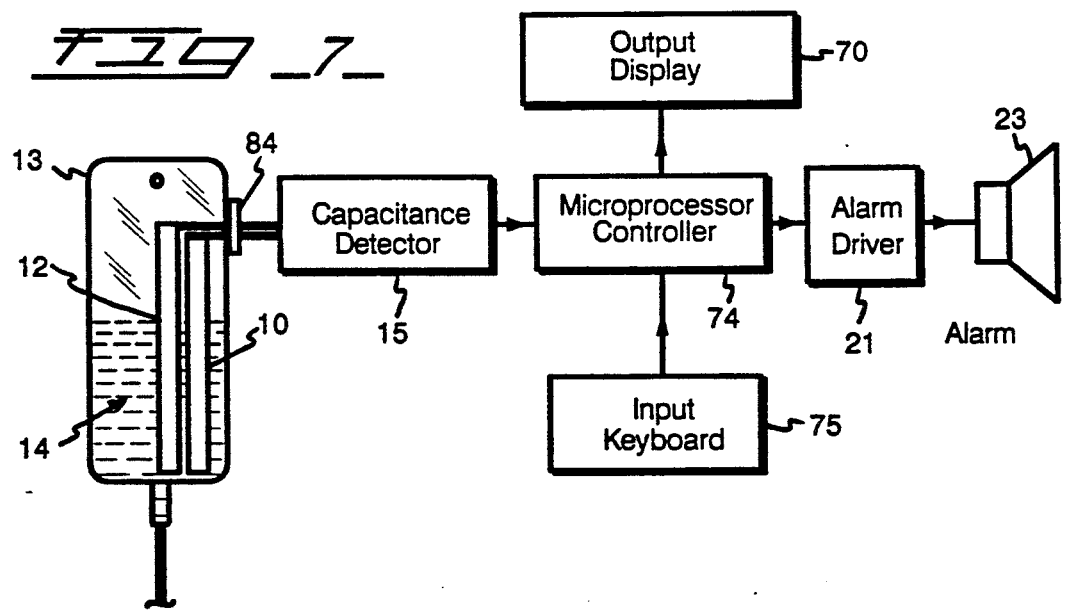

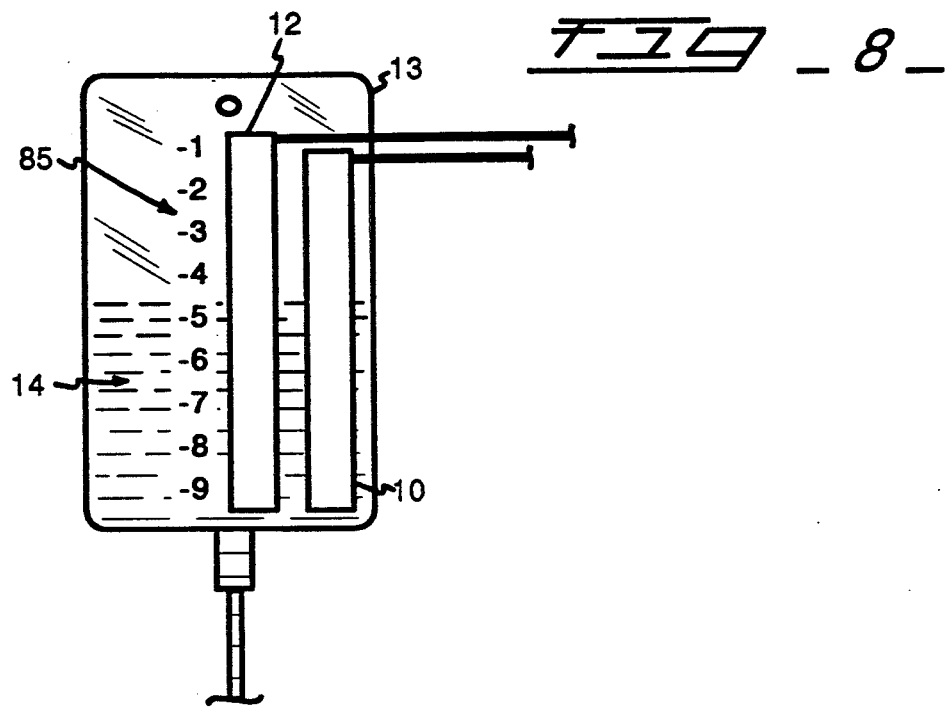
FIG_8_
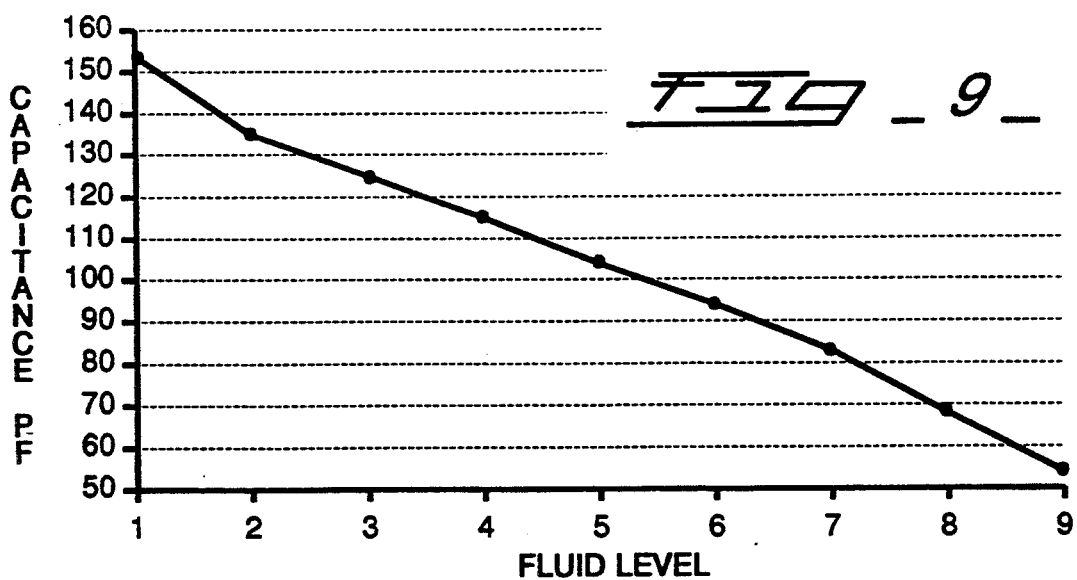
FIG_9_

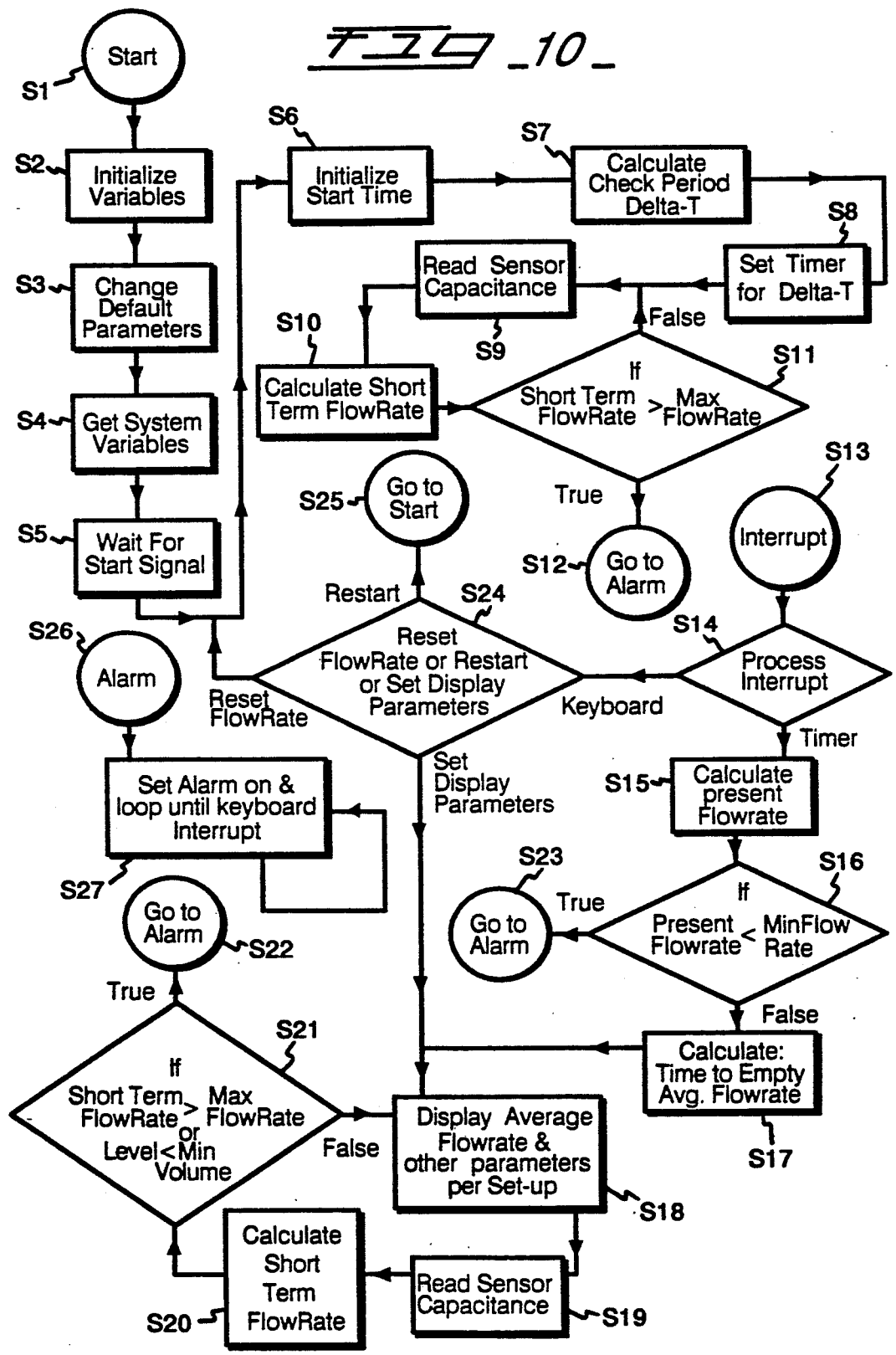

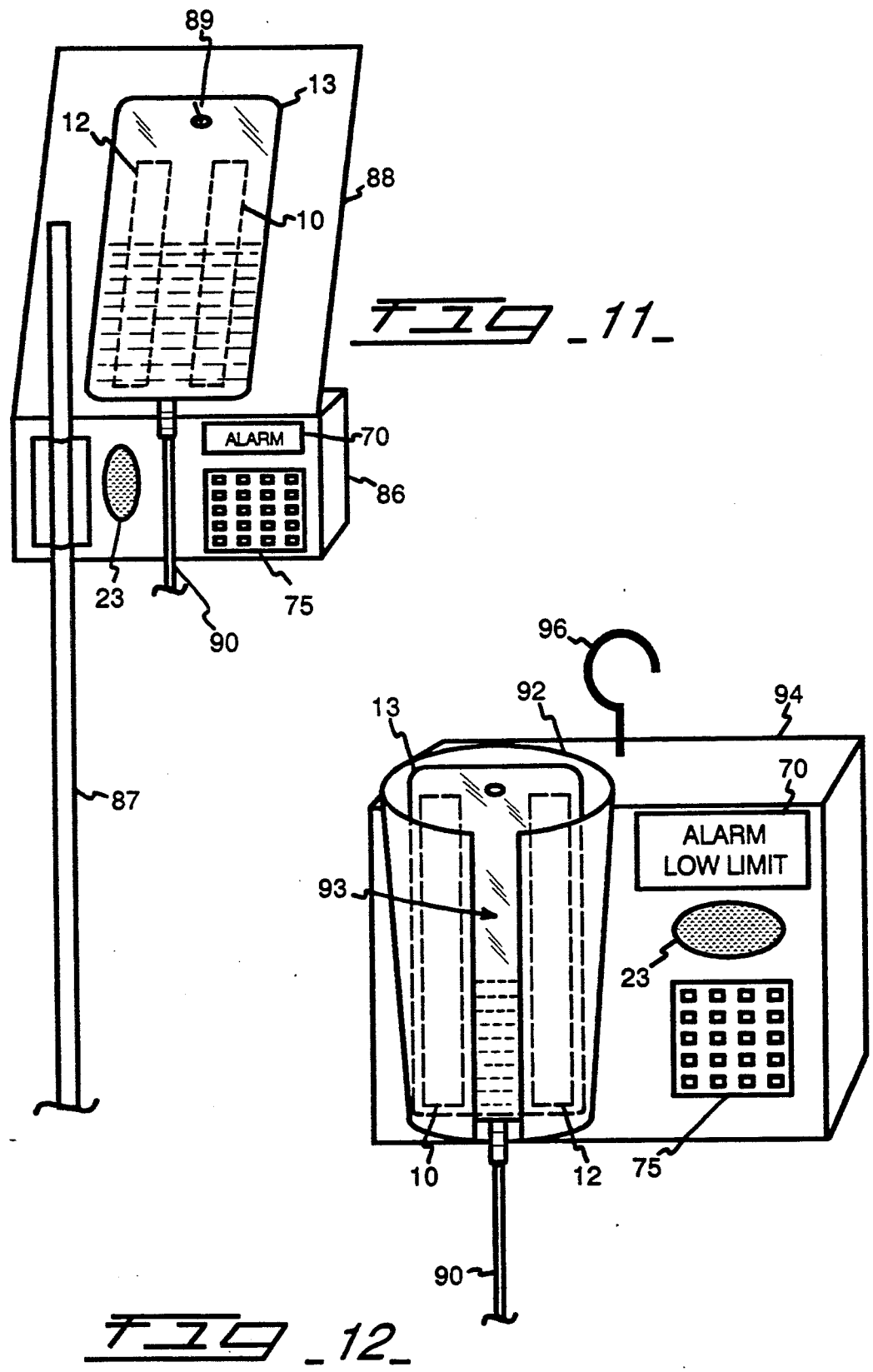

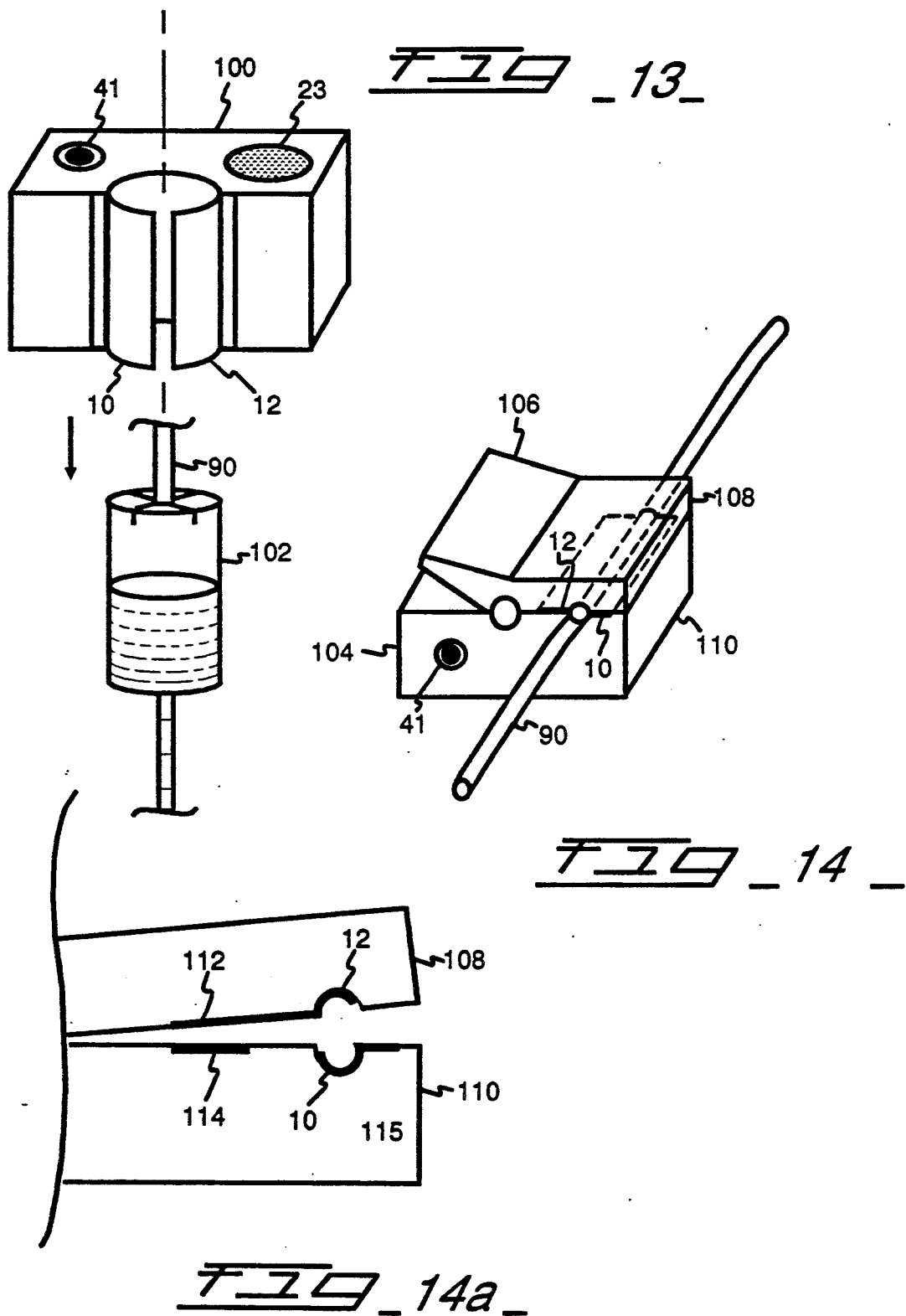

CAPACITANCE-TYPE FLUID LEVEL SENSOR FOR I.V. AND CATHETER BAGS

FIELD OF THE INVENTION

The present invention generally pertains to the field of capacitance-type fluid level sensors, and is more particularly directed to capacitance-type sensors which can be used to determine the fluid level and flow rate from or into a disposable container such as a flexible plastic bag used for intravenous (i.v.) injection, or a bag attached to a catheter used to collect body fluids.

BACKGROUND OF THE INVENTION

Disposable containers are used in many industries to hold and dispense fluids of various natures. When the fluid has been used and the container is empty, or when it is filled with waste, it is usually thrown away. Some examples of this type of packaging are flexible plastic i.v. and catheter bags commonly used in hospitals.

Sterile i.v. bags are normally used to dispense plasma, whole blood, replacement electrolyte, etc. The bags are usually imprinted or screen-labelled with the required documentation to identify the contents. When using containers of the i.v. bag type, the normal procedure is to dispense a metered amount over a given period of time by unmonitored, gravity-fed, drip feeding. The containers themselves come in different sizes, and i.v. fluids are administered to patients requiring widely varying flow rates. For example, 250 milliliter (ml.) to 1 liter plastic i.v. bags or bottles may be used to dispense a solution of 0.9% saline, Ringers lactate, 5% glucose, plasma, or blood to an adult over a 10–40 minute or longer time period, at rates of 1-25 ml. per minute (or more depending on the need).

It is a common practice to pre-set the gravity-driven flow rates via a visual drop-counting metering mechanism located above the i.v. needle. However, pre-set flow rates can vary over a substantial range, due to changing resistance to outflow resulting from several variables. Some of the variables that can affect the flow rate include: the changing height of the insertion site relative to the fluid level as the patient moves about; a partial or complete closing (kinking) of the tubing; the thrombosis (clotting) promoting propensities of the solution being dispensed; the angle of the needle influencing the occlusion of its bevelled opening; the settling of the various components of the fluid in the container, such as blood cells; and other reasons. Therefore, it has previously been difficult to predict with accuracy the exact time when all of the fluid will have been dispensed.

It is detrimental to a patient to have the flow of an i.v. fluid come to a complete stop, unattended, for any reason, because the i.v. fluid bag emptied unobserved before it was replenished. Complications which can occur after the flow has stopped include the clogging of the needle due to blood clotting, usually requiring reinsertion of a new needle, or blood passing out of the patient into the tubing. It is important to note that, in addition to pain, the risk of infection and hematoma increases every time a needle has to be inserted and reinserted into a vein.

Today the standard method of administering i.v. fluids is to count the number of drops falling in a drop chamber over a small time period to determine an estimated flow rate, and then calculate the approximate time required for the container to empty to a particular level. Someone, usually a nurse, must periodically monitor the i.v. bag in order to determine the time when the i.v. fluid level reaches the desired level for changing the bag. Under some circumstances, an expensive, complicated, electronic, motor-driven, peristaltic pump, costing $1,000-$5,000 dollars, must be used to precisely control the flow rate to a particular patient.

A need, therefore, exists to find a practical, low-cost solution to the problem of how to determine, without constant direct human observation, when the fluid in one of these containers reaches a level requiring action by the nurse, attendant, or patient. The present invention fills this need.

OBJECTS AND SUMMARY OF THE INVENTION

A primary object of the present invention is to provide the medical profession with an efficient, inexpensive way to continuously sense the fluid levels in bags used for dispensing an i.v. fluid or for collecting body fluids.

Another object of the present invention is to provide a visual and/or audible indication of the actual progress (or lack of progress) of the flow of the fluids to or from a plastic bag—before a problem arises.

Yet another object of the present invention is to provide a measuring system that is inexpensive, compact, and easy to attach and detach from the container.

A further object of the present invention is to allow some portions of the system to be disposable by having these portions of the fluid sensing mechanism integrated into the manufacturing or printing process of the container itself.

Still another object of the present invention is to provide a way to sense the level and determine the flow rate of sterile solutions without contaminating the fluid.

Accordingly, the present invention provides a capacitance-type fluid level sensing system for determining the amount of fluid in a container, for example, a disposable plastic bag used for intravenous infusion or the collection of biological fluids or other waste from a human body. In a preferred embodiment of the invention, conductive plates are positioned on the outside of the container and connected to a circuit for detecting any change in the capacitance of the capacitor formed thereby. The change in capacitance is due to the change in the dielectric constant of the combination of the container and fluid, due to the change in the fluid level therein. For some implementations, it is preferable that the conductive plates be applied directly to the bags, using a printing or screening process, at the same time as the normal identification markings are applied. Conductive inks can be utilized to implement this type of conductive plate to provide a low-cost solution to measuring the fluid level, while at the same time being disposable. However, the conductive plates could also be applied with adhesives, or held in contact with the fluid vessel using an external mechanical apparatus.

In one embodiment, when the fluid level in an i.v. bag decreases to a predetermined level, an audible annunciator is sounded to indicate that the level is becoming critically low. In another embodiment, when the fluid level in a bag collecting body fluids rises to a predetermined level, an audible annunciator is sounded to indicate the level is becoming critically high.

The device in its various embodiments can provide a visual display of the level, or can provide an audible alarm at the patient's bedside or at a remote location (e.g., a nurse's station). It can also be made to serve as a flow rate monitor to alert the nurse to increase or decrease the amount of fluid the patient is receiving.

In another embodiment, a microprocessor controller is provided to measure the change in capacitance from a series of individual conductive plates, and thereby activate an appropriate warning annunciator plus a visual display of information associated therewith. Moreover, a distributive conductive plate configuration may be used to advantage in sensing a continuous flow rate, rather than stepped monitoring of the fluid level. Alternative annunciation, detection, and display features are shown in various other embodiments.

In still another embodiment, a flexible plastic i.v. fluid or body fluid bag would be attached to a flat supporting panel having conductive plates mounted therein. The amount of fluid in the bag could then be monitored by the conductive plates, particularly if the bag support panel were slanted at a backwards angle such that gravity would hold the bag against the panel. In another embodiment using the same principal, a flexible plastic bag could be inserted within a container for support, wherein the container has the conductive plates mounted on an inside surface, such that gravity is used to hold the container against the plates.

A further embodiment provides capacitance-type fluid level sensing for the drip bulb used in i.v. infusion, wherein the conductive plates are configured to fit around the outside surface of the drip bulb. Finally, another embodiment of the invention provides a small sensing device which is adapted to clamp to the i.v. tubing much like a clothes pin attaches to a clothes line. The small sensing device incorporates conductive plates on the inside surface of the clamp which are connected to an alarm circuit designed to annunciate when an air/liquid interface appears within the tubing.

Thus, the present invention in its different embodiments provides an easy-to-use, inexpensive, portable capacitance-type fluid level sensing device which can be installed in every hospital room, ambulance, or mobile medical facility. The invention could also be of great use in military battlefield and refugee situations. The immediate advantages of using such a fluid level sensor would include reduced patient concern about the i.v. or catheter status, as well as increasing productivity for the medical professionals directly involved in the monitoring of these fluids. Furthermore, the energy source necessary to power this device is not dependent on connection to an alternating current source, making the device completely portable.

BRIEF DESCRIPTION OF THE DRAWINGS

These and other objects, features, and aspects of the invention will be better understood and more fully described upon reading the following detailed description in conjunction with the appended drawings wherein:

FIG. 1 is a block diagram of a system for determining the fluid level in a disposable container of the i.v. bag type in accordance with the present invention;

FIG. 2 is a rear view of a capacitance-type fluid sensor alarm enclosure containing all the elements identified in the block diagram of FIG. 1;

FIG. 3 is a front view of the capacitance-type fluid sensor alarm enclosure of FIG. 2 placed in contact with a disposable i.v. bag;

FIG. 4 is a detailed circuit diagram of the capacitance sensing circuitry for the system illustrated in FIG. 1;

FIG. 5 is a waveform diagram illustrating various electrical signals of the circuit of FIG. 4;

FIG. 6 is a block diagram of another embodiment of a system for determining a plurality of fluid levels, constructed in accordance with the present invention;

FIG. 7 is a block diagram of still another embodiment of the system for continuously determining fluid levels, also constructed in accordance with the present invention;

FIG. 8 is a pictorial representation of a disposable container having a graduated scale disposed along the length of the capacitor conductive plates;

FIG. 9 is a graphical representation of capacitance as a function of fluid level for the i.v. bag illustrated in FIG. 8;

FIG. 10 represents a flowchart for the microprocessor controller used in the system of FIG. 6 or FIG. 7, illustrating the specific sequence of operations performed in accordance with the practice of this embodiment of the invention;

FIG. 11 is a pictorial representation of another embodiment of a capacitance-type fluid level sensor which is designed to support the i.v. bag;

FIG. 12 is a pictorial representation of another embodiment of the invention, illustrating a different support mechanism for the i.v. bag;

FIG. 13 is a pictorial representation of a capacitance-type fluid level sensor adapted to be mounted on the external surface of an i.v. drip tube; and FIGS. 14 and 14A are pictorial representations of a clamp-type apparatus adapted to directly attach to the i.v. injection tubing.

DETAILED DESCRIPTION OF THE INVENTION

Referring now to FIG. 1, a capacitance-type fluid level sensing system constructed in accordance with the present invention is shown. A container 13, preferably a disposable plastic i.v. or catheter bag, bottle, or the like, has two relatively closely-spaced external conductive plates 10, 12 disposed thereon. Because the bag 13 (typically plastic) and fluid 14 (generally an electrolyte solution) form a dielectric which varies as the fluid level changes, the capacitance apparent between the two plates will vary in accordance therewith. It is readily apparent that conductive plates of this type may be affixed to containers of plastic, glass, or other materials by a number of conventional techniques to produce similar results. Moreover, plates which are mounted to an external apparatus could also be placed in contact with the container, as will be seen below.

The two conductive plates 10, 12 are of dimensions to produce electric field lines through the container 13 and the fluid 14 therein, such that the plates serve as the plates of a capacitor. Depending on the type of container and fluid used, the conductive plates 10, 12 may be constructed in the shape of thin wires, rectangular plates, or even circular dots. In fact, one of the conductive plates 10 may be constructed as a conductive coating covering almost the entire surface of the bag, wherein the other plate 12 would be positioned where the conductive coating is absent. In some of the embodiments, the conductive plates are applied directly to the bags, using a conductive ink printing or screening process at the same time as the normal identification markings are applied. However, the conductive plates could also be applied with adhesives, or manufactured as part of the sidewall of the bag, or held in contact with the fluid vessel using an external mechanical apparatus.

The conductive plates 10, 12 are connected to circuitry to determine the fluid level based on the changing capacitance. A capacitance detector 15 converts this capacitance variation apparent at conductive plates 10, 12 into an electric signal, typically an analog voltage signal, which is representative of the change. This voltage or other signal is compared, in a comparator 17, with a reference signal provided by a sensitivity reference 19. The reference signal is indicative of a capacitance value corresponding to a particular fluid level. The sensitivity reference signal may be generated from various sources, but preferably is an analog voltage which is adjustable by a potentiometer.

When the fluid level in the i.v. (or catheter) bag is drained below (or filled above) the threshold set by the reference level, the comparator 17 will output an alarm signal to an alarm driver 21. The alarm driver 21 will condition the alarm signal to drive an annunciator or alarm 23 with the signal. The alarm driver could include an operational amplifier driving a piezoelectric buzzer, or an oscillator driving a speaker. However, the alarm driver 21 could also condition the alarm signal to be routed to a remote location, such as a nurse's station, without producing an audible indication at the fluid level sensing device itself.

For an i.v. bag, the sensitivity reference signal is set to represent the capacitance apparent when the i.v. bag is at a level where it has almost run dry. The alarm will then sound when the bag is emptied to that level. Alternatively, if the bag is a catheter bag, then the sensitivity reference is set to the capacitance of a full bag. The comparison is inverted, and the alarm will then sound when the bag is filled to that level. This comparison inversion could be accomplished by a selector switch, such that the same fluid level sensing device could be used for both types of bags.

FIG. 2 illustrates a rear view of one embodiment of how the capacitance-type fluid level sensor can be packaged. The enclosure 11 contains two conductive plates 10, 12 making up the sensing capacitor, while the capacitance sensing electronics and the audio alarm 23 are mounted to a printed circuit board contained within enclosure 11. A power source, such as a standard 9-volt alkaline battery, would also be contained within or affixed to enclosure 11.

FIG. 3 illustrates how the sensor enclosure 11 can be placed in contact with the i.v. fluid bag 13 so as to trigger on a low fluid level state. If the enclosure 11 is constructed to have conductive plates 10, 12 attached on its rear side as an integral part of the enclosure, then affixing the enclosure next to the plastic i.v. bag 13 (as shown), via adhesive or some other mechanical arrangement, would suffice to form the required capacitor using the fluid as the dielectric. On the other hand, if i.v. bag 13 already has conductive plates 10, 12 screened on an outside surface thereof, then electrical contacts or wires can be used to connect the two screened-on conductive plates to the capacitance detector circuitry within the enclosure 11. The enclosure could then be mounted on or near the bag 13, or could be mounted on a nearby structure and connected by wires. In either case, the level at which the capacitance-type fluid level sensor would trigger would be located approximately between the two horizontal plates 10, 12, as indicated by the arrow in FIG. 3.

The circuit diagram of a preferred embodiment of the capacitance-type fluid level sensor is shown in FIG. 4. The primary function of the capacitance detector circuitry is to sense variations in the dielectric constant of the container as caused by the difference in the fluid levels therein. As shown in FIG. 4, the circuit includes a first conductive plate 10 which is suitably attached to the outside wall of the container 13 which holds the fluid 14. A capacitor is formed by plate 10 and a second plate 12, which is referenced to a voltage, more particularly ground. The conductive plate 10 is connected to a reference terminal $TR_1$ of a first monostable multivibrator 16. A second monostable multivibrator 18 is also provided. An oscillator 20, such as, for example, a well-known dual-invertor R-C network, is connected to provide a triggering signal to the trigger inputs T of both multivibrators simultaneously at a set periodic rate.

The conductive plates 10, 12 provide a variable time constant depending upon their capacitance and the dielectric between them, by being connected to one side of a voltage divider potentiometer 22 through resistor 24. A second time constant is developed at the $TR_2$ input of monostable 18 by being connected to a reference capacitor 28 through the other side of the divider 22 and resistor 26.

The monostables 16, 18 provide inverted-$Q_1$ and $Q_2$ outputs, respectively, to a NOR gate 32 which drives the base of an NPN transistor 36 through resistor 34. The NPN transistor has its collector coupled to a source of positive voltage $+V$, and its emitter coupled to the parallel connection of a capacitor 38 and a resistor 40 whose other terminals are grounded. The output of the transistor 36 at its emitter is a capacitance signal $C_S$. The output signal $C_S$ would then be coupled to a comparator input of an appropriate alarm device 44, such as a piezoelectric transducer circuit. The source of positive voltage $+V$ is provided by an on/off switch 44 and a battery 42, which may be a standard 9-volt alkaline battery.

The waveforms of FIG. 5 will now be fully described with reference to the circuit of FIG. 4. Time A of the waveforms 50 and 52 indicates the occurrence of one pulsed input signal from oscillator 20 to the T inputs of the monostables 16, 18. The monostables 16, 18 turn on to conduct at time A as indicated by the waveforms 50, 52, which represent the timing input signals $TR_1$, $TR_2$, respectively. Thus, at the time the monostables 16, 18 are triggered, the waveforms 50, 52 drop to their zero levels, and the R-C timing circuits allow the waveforms to rise exponentially in a positive direction towards a threshold level 54. The time constant of the exponential rise for monostable 16 is determined by the capacitance between plates 10, 12, and the resistor 24 in combination with potentiometer 22. Similarly, the reference capacitor 28 and resistor 26 form the timing circuit in combination with the potentiometer 22 to determine the time constant for the monostable 18.

Thus, it can be seen that the time constant of the monostable 18 is constant, since the reference capacitor 28 is invariant. However, because the capacitance between the plates 10, 12 varies with the dielectric constant of the material between them, the time constant of the monostable 16 can change. A time difference can occur between the time the input signal 50 of monostable 16 and the input signal 52 of monostable 18 reaches the threshold 54, as indicated by the times B and C.

In the particular example of the waveforms shown in FIG. 5, waveform 50 takes longer to rise to the threshold level 54, indicating that its R-C time constant is greater due to the capacitance between plates 10, 12 being greater than the capacitance of reference capacitor 28. At the time the threshold voltage 54 is reached by each monostable input timing signal, the respective monostable output signals 56 and 58 will change. At the time B, when the input signal 52 of the monostable 18 reaches the threshold level, the output signal 58 of that monostable will be reduced to zero. Afterwards, when the input signal 50 of monostable 16 reaches the threshold level at time C, the output signal 56 of monostable 16 goes positive.

For the detection of changes in the time constant of the two monostable output signals 56 and 58, the signals are fed to the input terminals of the NOR gate 32. When the outputs from the monostables are both below the logic switching level of the NOR gate, i.e., during the time between the respective level changes of the monostable signals, an output pulse 60 is produced at the base of the NPN transistor 36. The peak of the waveform 60 extends above the level 62 which represents the threshold voltage of the base-emitter junction of the transistor. This pulse 60 causes the transistor 36 to conduct, for a short period of time, to pulse current into the capacitor 38. The capacitor 38 is connected in parallel with the resistor 40, which is of a relatively high resistance to allow the charge on the capacitor 38 to dissipate slowly. Thus, as the capacitance of the plates between the plates 10, 12 varies, the analog voltage $C_S$ will vary in dependence thereon.

In the specific waveform example shown in the Figure, this positive pulse 60 indicates that more capacitance is present between plates 10, 12 than provided by reference capacitor 28. If this signal were applied to a comparator input of the alarm 44 through transistor 36, the alarm would indicate when the level of the fluid 14 in the container 13 has reached a point on the bag that has been designated to represent a full bag.

FIG. 6 illustrates another embodiment of a capacitance-type fluid level sensing system constructed in accordance with the invention. The system has a similar arrangement to that shown and described for FIG. 1, in that it includes a capacitance detector, an alarm driver 21, and an alarm 23. However, instead of only one capacitance sensor, this embodiment utilizes an array of discrete multiple sensors and multiple detectors 76. Each sensor is formed of one conductive plate 80 from a first column, and a second plate 82 from a second column. The multiple plate connections are brought to a connector 84 where the electronic circuitry can interface with the multiple sensors.

Associated with each pair of conductive plates 80, 82 is a capacitance detector which outputs a signal as its trigger point is reached. The multiple capacitance detectors 76 provide individual output signals to a microprocessor controller 72. The controller 72 can then read into its memory the multiplicity of capacitance signals from the detectors to determine the fluid level. Furthermore, an output display 70 provides considerable flexibility in deriving information from the capacitance detector. Depending upon the type of microprocessor controller hardware used, i.e., whether it has an internal analog-to-digital converter, input signals to the processor may be provided directly thereto.

The system of FIG. 6 provides a stepped sensing of the fluid level as the fluid level passes each pair of conductive plates 80, 82. The more sensors that are provided, the more discrete levels can be sensed. The microprocessor controller 72 can also calculate and display the status of a variety of functions, including time-averaged flow rate, estimated time-to-empty, the present volume remaining, and other data via the output display 70. The display information can also include the time when the i.v. was started, and what the recommended prescription was for the patient. The system can also be used to set the audible alarm 23, or to provide visual alarm through the display for detrimental changes in flow rate.

FIG. 7 illustrates an alternative embodiment of a capacitance-type fluid level sensor system constructed in accordance with the invention. In this embodiment, the array of discrete capacitors is replaced with a distributed capacitor which provides a continuous measurement of capacitance level versus volume. This embodiment is particularly adapted to be used with i.v. bags in which the sensing capacitor is screened or printed directly onto the bag, since the volume of the bag is known and the placement of the screened-on plates remains consistent from one bag to another. Microprocessor controller 74 would continuously perform calculations to determine the fluid level as a function of the capacitance. Calculations can also be performed by the microprocessor controller 74 so that the alarm can be turned on or off as desired. The controller 74 also provides humanly discernable information to the user via the output display 70. The output display function can be based on a number of different needs, including a time-averaged flow rate, estimated time-to-empty, the present volume remaining, etc. An input keyboard 75 provides a means for the user to input information into the controller in response to the processor inquiries provided on the output display 70.

FIG. 8 illustrates a flexible container 13 with a graduated scale 85 printed or screened on the container next to the conductive plates 10, 12. The scale 85 corresponds to the different fluid levels 14 in the container which are shown graphically in FIG. 9.

The graph of FIG. 9 discloses that a relatively linear relationship exists between the capacitance (measured in picofarads) and the fluid level in the container 13 (measured by the graduated scale 85). Hence, by using this data or a representative linear equation, the fluid level sensing system can be calibrated. Moreover, if the total volume of the bag is known, then the flow rate in milliliters/minute or milliliters/hour can be calculated as a function of the change in level. The container and solution used for this calibration was a standard plastic one liter i.v. bag of Ringers Lactate solution having conductive plates measuring 0.38 inches in width, 11.50 inches in length, and 0.10 inches apart, and were vertically disposed on the bag as shown in FIG. 8.

Referring now to the flowchart of FIG. 10, the specific sequence of operations performed by microprocessor controller 72 or 74, of FIGS. 6 or 7, is shown in accordance with the practice of these embodiments of the invention. The primary difference in the flowchart operation from controller 72 to controller 74 is that controller 72 would store the multiplicity of capacitance signals from the individual detectors, and use these stored values to determine a continuous change in fluid level over time, as supposed to controller 74 being able to continuously perform calculations on the input signal itself to determine the fluid level. However, microprocessor controller 74 can also be programmed to store the input values directly, and calculate the fluid level from the stored values, in the same manner as required by the use of multiple capacitance detectors. In fact, it may be desirable that a single program, which stores its input values, be used for either type of system, i.e., the array of discrete multiple sensors of FIG. 6, or the continuous fluid level sensing plates of FIG. 7. In either case, a Motorola MC68HC11, could be used for microprocessor controllers 72 or 74.

The program operation begins at the start step S1. At step S2, all program variables are initialized, the alarm and display outputs reset, and the interrupt vectors of the processor are set up. In step S3, the processor performs a subroutine to change the default parameters of the system. This subroutine would consist of providing output signals to the display such that the system user is asked questions regarding the optional setting or resetting of the operational default parameters, which would not typically need to be changed for each use. These default parameters would include: how the alarm should trigger (i.e., when the bag is full or when the bag is empty); the type of alarm desired (e.g., tones, digitized voice message, visual only, etc.); the type of output display (i.e., if the display is to toggle between the flow rate display and an estimated time-to-empty display); the time of day; etc. Once the user inputs this information via input keyboard 76, the controller subroutine changes the default parameters. Step S3 is entirely optional, as the step would not be required unless the particular application has changed. For purposes of clarity, the remaining steps of the flowchart are only described in terms of monitoring the flow from an i.v. bag.

In step S4, the controller obtains the system variables from the user, which would typically change for the same application. A similar subroutine would be performed to display information and read the keyboard entry for this information provided by the user. The system variables would include such parameters as: the level at which the bag is considered to be empty (or full); the flow rate that would be considered an allowable minimum or maximum; the volume of the bag; etc.

The control of the processor then proceeds to step S5, wherein the processor waits for an external start signal from the keyboard (or other input) in order to start monitoring the fluid level. In step S6, the processor records the start time to initialize the flow rate calculation procedure. The processor then calculates the check period in step S7, i.e., the period of time in which the program will update its flow rate calculations. If the flow rate is very low, then a longer check period is used, because otherwise too small of a difference capacitance would be observed by the microprocessor. Similarly, a shorter check period is set if the flow rate is relatively high. In step S8, the processor's internal countdown timer is set to request an interrupt after the check period (delta t) has expired.

The sensor capacitance is read in step S9. If the capacitance signal is represented as an analog voltage level, such as that generated at $C_S$ of FIG. 4, then reading the sensor capacitance into the processor would simply consist of reading the internal analog-to-digital converter of the processor. On the other hand, if the capacitance signal is a preconditioned digital pulse having a predetermined pulse width, as would be provided at the output of the circuit of FIG. 4 if capacitor 38 were removed, then a loop-counting subroutine or internal timer could be used to measure the pulse width.

In step S10, the instantaneous or short-term flow rate is calculated. The flow rate calculation is performed by determining the change in volume from the measured change in level of the bag, and dividing it by the measuring time period. Hence, the short-term flow rate is determined from the change in measured fluid level over less than a single check period, i.e., less than one delta t. In step S11, the calculated short-term flow rate established in step S10 is compared against the maximum flow rate derived from the system variable input subroutine of step S4. If the calculated short-term flow rate is greater than the maximum flow rate, then an alarm subroutine (described below) is called at step S12. This would be the case if, for example, the i.v. needle were dislodged—a case in which it is important to immediately trigger an alarm without waiting for averaging calculations to be performed over a longer period of time. If the calculated short-term flow rate is less than the allowable maximum, then the program continues to loop through steps S9, S10, and S11, continuously monitoring the capacitance, until an interrupt occurs from either the expiration of the internal timer set in step S8, or a keyboard interrupt subroutine.

Once an interrupt has occurred in step S13, the interrupt is processed in step S14 to determine whether or not the interrupt was from a timer expiration or a keyboard input. If the interrupt timer has expired, which occurs after every check period delta t, then the present flow rate is calculated in step S15 in essentially the same manner as it was done in step S10. The present flow rate is calculated from the change in measured fluid level over the last check period, i.e., exactly one delta t. The newly-calculated present flow rate is compared to the minimum defined flow rate in step S16. If the present flow rate is less than the allowable minimum, then the alarm subroutine is again called in step S23. This would be the case if, for example, the i.v. tube were kinked and no fluid was being dispensed. If no such problem exists, control proceeds to step S17.

New system status parameters are calculated in step S17. More specifically, a time-averaged flow rate is calculated by maintaining a running average of the present flow rate calculations. An estimated time-to-empty is then determined by dividing the total volume by the average flow rate. Similarly, the estimated time of day at which the bag should be empty would be calculated by adding the present time of day to the estimated time-to-empty. The volume of the fluid dispensed, or the volume of fluid remaining, can also be calculated per the relationship defined in FIG. 9.

The display subroutine of step S18 displays any or all of the system status parameters, the system variables, or the default parameters. For example, the display may be programmed to toggle between the average flow rate and the estimated time-to-empty. Any of the other parameters could also be displayed as desired. The display routine at step S18 would be encountered after the first time an interrupt has occurred. The information remains on the display until the occurrence of a later interrupt.

In step S19, the main loop of the system begins by again reading the sensor capacitance as was done in step S9. The short-term flow rate is again calculated in step S20 as was done in step S10, and the fluid level is again determined using the look-up table. In step S21, the short-term flow rate is compared with the maximum flow rate, and the alarm subroutine is called in step S22 if the limit is exceeded. Similarly, the instantaneous fluid level, i.e., the fluid level corresponding to the sensor capacitance just measured, is compared with the defined low level volume threshold parameter, and the alarm routine is called if the level is too low. This would occur if the bag was near empty. Otherwise, control proceeds to re-display the appropriate parameters in step S18, and re-enter the main loop until an alarm is triggered or an interrupt occurs.

If the interrupt processed in step S!4 is a keyboard request, then the processor determines what type of action is required by the user. For example, if a system reset is requested, control proceeds to step S25 wherein the processor is reset and operation returns to the start at step S1. On the other hand, if the user requests a particular parameter to be displayed, then control proceeds to step S18 to display the appropriate parameter. Finally, if an intentional adjustment to the flow rate has been made externally by the user, via the i.v. tube metering mechanism, for example, then control proceeds to step S6 to re-initialize the start time.

In the alarm subroutine beginning at step S26, the particular type of alarm, as defined in the default parameters, is triggered in step S27. Control proceeds to loop in the alarm subroutine until a keyboard interrupt is detected at step S24 due to the user desiring to reset the alarm. Upon this type of keyboard interrupt, the alarm would be reset and step S25 would restart the program.

Referring now to FIG. 11, another embodiment of the present invention is disclosed, wherein the capacitance-type fluid level sensor is constructed as a self-contained enclosure 86 mounted to a vertical support 87. A slanted vertical panel 88 is used to support bag 13 by suspending the bag from its hook support aperture 89. The panel 88 incorporates a sensing capacitor formed of conductive plates 10, 12 constructed as an integral part of the panel front surface. The panel 88 is slanted slightly to the rear as shown. This rearward angle allows gravity to assist in maintaining proper contact between the conductive plates and the sidewall of the bag.

FIG. 12 illustrates a further embodiment of the present invention, wherein the flexible plastic bag 13 is disposed within an external support container 92 having a shape of an inverted fulcrum of a cone. The i.v. tube 90, extending from the bottom of bag 13, would be threaded through the gap 93 of the container 92, such that the fluid can properly be dispensed from the bag. The enclosure 94, which houses the display 70, the alarm 23, and the keyboard 75, is affixed to an outside wall of container 92 as shown. The conductive plates 10, 12, preferably disposed on the inside surface of container 92, would be connected to the front of enclosure 94 via wires or electronic connectors. The weight of the fluid in the bag, pressing against the sides of the enclosure, would maintain the bag against the conductive plates. The entire apparatus can then be supported by a single bag support hook 96. Note that a modified version of this embodiment could be designed to accommodate bottles having non-flexible sidewalls.

A further embodiment of the invention is shown in FIG. 13, wherein the capacitance-type fluid level sensing system is self-contained in enclosure 100 which is adapted to fit around the outside surfaces of a conventional i.v. drip tube 102. The conductive plates 10, 12 would be formed to have a curved surface which conforms with the outer cylindrical surface of the i.v. drip tube. Two vertical conductive plates 10, 12 could be used as shown in FIG. 13. In the alternative, two horizontal conductive plates could be used to detect a specific fluid level, as shown in FIGS. 2 and 3, or an array of discrete conductive plates 80, 82 could also be used as shown in FIG. 6.

FIG. 14 illustrates a further embodiment of the invention, wherein the entire fluid level sensor is enclosed within a miniaturized clamp-type housing 104 which is adapted to be clamped onto the i.v. tube 90 in much the same manner as a clothespin is clamped to a clothesline. A spring-action lever 106 is used to open the jaws 108, 110, such that the device can be securely clamped onto the i.v. tube 90. The conductive plates 10, 12 are disposed on the inside surfaces of the jaws 108, 110, as shown in FIG. 14A. Preferably, the conductive plate 12 located in the outer jaw 108 would have an extension 112 which mates with contact 114 on the inner jaw 110 when the clamp is closed. In this manner, electrical contact is established to the outer conductive plate 12 without requiring additional wiring or rotating contacts. Electrical connections are then made to contact 114 and the extended portion 115 of contact 10, as shown. Note also that the conductive plates 10, 12 are formed in a curved shape which is somewhat less than a semicircle, such that the contacts lo, 12 do not touch when the jaws are closed.

In review, it can now be seen that the capacitance-type fluid level sensor of the present invention provides an inexpensive, easy-to-use, self-contained device having numerous applications. Each of the various embodiments described above provide particular advantages in various applications of fluid level sensing. Moreover, the invention can be used to determine the liquid level of any liquid reservoir or conduit, particularly where internal capacitance sensors are prohibited due to potential contamination of sterile solutions.

While preferred embodiments of the invention have been illustrated, it will be obvious to those skilled in the art that various modifications and changes may be made thereto without departing from the spirit and scope of the invention as hereinafter defined in the appended claims.

What is claimed is:

1. A fluid level sensing system having capacitance sensing means for determining whether a particular fluid level has been reached in a container used for introducing or removing fluids to or from the human body, said system comprising:
   a substantially enclosed container having means for introducing or removing fluids to or from the human body, said container further having nonconductive sidewalls and at least one port for increasing or decreasing the level of fluid in said container;
   a capacitor formed of at least two conductive members positioned at a particular location adjacent the external surface of said container such that said members cannot directly contact fluid in said container and such that the capacitance of said capacitor changes as the level of fluid in the container varies above or below said particular location;
   means for detecting changes in the value of said capacitor resulting from changes in the level of fluid, and for generating a capacitance signal in response thereto;
   means for providing a reference signal indicative of a capacitance value corresponding to a particular fluid level;
   means for comparing said capacitance signal with said reference signal, and for generating an output signal in response to the difference between said capacitance signal and said reference signal; and means for providing an indication in response to said output signal that said particular fluid level in said container has been reached.

2. The fluid level sensing system according to claim 1, wherein said container is a disposable plastic bag having flexible sidewalls.

3. The fluid level sensing system according to claim 2, wherein said container is an intravenous injection bag.

4. The fluid level sensing system according to claim 2, wherein said container is a catheter bag.

5. The fluid level sensing system according to claim 1, wherein said container includes a tube connected to said port, and wherein said conductive members are affixed at a particular location to the external surface of said tube.

6. The fluid level sensing system according to claim 5, wherein said tube includes a drip tube.

7. The fluid level sensing system according to claim 1, further comprising housing means for enclosing electronic circuitry, wherein said housing means includes said two conductive members constructed as an integral part of at least one surface of said housing such that said housing is adapted for being directly affixed to an outside surface of said container.

8. The fluid level sensing system according to claim 1, wherein said two conductive members are printed or screened directly onto the outside of said container.

9. The fluid level sensing system according to claim 1, wherein said detecting and generating means comprises:
   an oscillator producing periodic trigger signals;
   a first monostable triggered by said trigger signals and generating pulses having a duration determined by a reference capacitor;
   a second monostable triggered by said trigger signals and generating pulses having a duration determined by the capacitance of said capacitor formed of said two conductive members; and
   means for comparing the duration of said pulses from said first and second monostables, and for generating a capacitance signal representative of that difference.

10. The fluid level sensing system according to claim 1, wherein said comparing and generating means includes a microprocessor.

11. The fluid level sensing system according to claim 10, wherein said microprocessor is programmed to calculate the flow rate of the fluid to or from said container.

12. The fluid level sensing system according to claim 11, wherein said microprocessor is programmed to calculate both a short-term flow rate and a time-averaged flow rate.

13. The fluid level sensing system according to claim 1, wherein said indication providing means includes a visible display.

14. The fluid level sensing system according to claim 1, wherein said indication providing means includes an audible alarm.

15. The fluid level sensing system according to claim 1, wherein each of said two conductive members of said capacitor is formed of a plurality of conductive metal strips.

16. The fluid level sensing system according to claim 1, wherein said capacitor is formed of only two metal strips positioned generally parallel and vertical.

17. An electronic device for sensing fluid levels in an intravenous injection or catheter administering apparatus, said apparatus constructed of nonconductive material, said electronic device comprising:
   means for housing electronic circuitry, said housing means including conductive plates constructed as an integral part of at least one surface of said housing, said housing adapted for positioning said conductive plates on an outside surface of said apparatus to form a capacitor such that the capacitance of said capacitor changes as the level of fluid varies in the apparatus;
   means for detecting changes in the value of said capacitor resulting from changes in the level of said fluid, and generating a capacitance signal in response thereto; and
   means for providing an indication in response to said capacitance signal that said particular fluid level in said container has been reached.

18. The electronic device according to claim 17, wherein said detecting means further comprises:
   means for measuring the value of said capacitor resulting from changes in the level of said fluid, and for generating a capacitance signal in response thereto;
   means for providing a reference signal indicative of a representative capacitance value corresponding to a particular fluid level; and
   means for comparing said capacitance signal with said reference signal, and for generating an output signal in response to the difference between said capacitance signal and said reference signal.

19. The electronic device according to claim 17, wherein said indication providing means further comprises means for providing an alarm signal when said particular fluid level in said container has been reached.

20. The electronic device according to claim 17, wherein said electronic device is portable, battery-powered, and entirely enclosed within said housing, said housing including two conductive plates constructed as an integral part of the rear surface of said housing such that said electronic device is adapted for affixing directly to an outside surface of an intravenous injection or catheter bag or bottle.

21. The electronic device according to claim 17, wherein said housing includes a panel having a substantially flat and inclined shape, said housing including two conductive plates constructed as an integral part of a surface of said panel such that said two conductive plates contact an outside surface of an intravenous injection or catheter bag or bottle when it is positioned against said panel.

22. The electronic device according to claim 17, wherein said housing includes a frame having the substantial shape of an inverted frustrum of a cone, said housing including two conductive plates constructed as an integral part of the inner surface of said frame such that said two conductive plates contact an outside surface of an intravenous injection or catheter bag or bottle when it is positioned within said frame.

23. The electronic device according to claim 17, wherein said housing includes a frame having the substantial shape corresponding to the outside surface of an intravenous injection drip tube, said frame including two conductive plates constructed as an integral part of the inner surface of said frame and adapted to contact an outside surface of said drip tube when said drip tube is positioned within said frame.

24. The electronic device according to claim 17, wherein said housing includes means for clamping said housing to a portion of said intravenous injection or catheter administering apparatus, said clamping means including two conductive plates constructed as an integral part of the inner surface of said clamping means such that said two conductive plates contact an outside surface of said apparatus when said clamping means is positioned over said apparatus.

25. An apparatus for dispensing or accumulating fluids to or from a human body, said apparatus comprising:
a substantially enclosed container having nonconductive sidewalls and at least one port for increasing or decreasing the level of fluid in said container;
tube means, coupled to said port, for dispensing or accumulating fluids to or from a human body; and
at least two conductive members affixed at a particular location to the external surface of said apparatus thereby forming a capacitor, said conductive members constructed and arranged such that said members cannot directly contact fluid contained within said apparatus, and such that the capacitance of said capacitor changes as the level of fluid in the apparatus varies above or below said particular location.

26. The apparatus according to claim 25, wherein said container is a disposable plastic bag having flexible sidewalls.

27. The apparatus according to claim 26, wherein said container is an intravenous injection bag.

28. The apparatus according to claim 26, wherein said container is a catheter bag.

29. The apparatus according to claim 25, wherein said two conductive members are printed or screened directly onto the outside of said container.

30. The apparatus according to claim 25, wherein said conductive members are affixed at a particular location to the external surface of said tube means.

31. The apparatus according to claim 25, wherein said tube means includes a drip tube.

32. The apparatus according to claim 25, wherein said two conductive members are constructed and arranged as two generally parallel strips of metal positioned substantially horizontally across a portion of said apparatus, said two strips being positioned such that the separation between them is located approximately at a position representing a fluid level wherein the fluid in said apparatus would be considered to be at a low level.

33. The apparatus according to claim 25, wherein said two conductive members are constructed and arranged as two generally parallel strips of metal positioned vertically down a portion of said apparatus, said two strips extending from an upper portion of the apparatus at a position representing a fluid level wherein the fluid in said apparatus would be considered to be at a high level, and extending to a lower portion of the apparatus at a position representing a fluid level wherein the fluid in said apparatus would be considered to be at a low level.

34. The apparatus according to claim 25, wherein said apparatus further includes a plurality of pairs of conductive members, each of said pairs of members forming a discrete capacitor, said members extending from an upper portion of the apparatus at a position representing a fluid level wherein the fluid in said apparatus would be considered to be at a high level, and extending to a lower portion of the apparatus at a position representing a fluid level wherein the fluid in said apparatus would be considered to be at a low level.

35. The apparatus according to claim 25, further comprising means for detecting changes in the value of said capacitor formed by said conductive members, said detector means contained in an enclosure which is affixed to the outside of said apparatus.

36. A method for detecting fluid levels in an intravenous injection or catheter apparatus, said apparatus constructed of nonconductive material, said method comprising the steps of:
(a) providing conductive members on an outside surface of said apparatus to form a capacitor such that the capacitance of said capacitor changes as the level of fluid varies in the apparatus;
(b) detecting changes in the value of said capacitor resulting from changes in the level of said fluid, and generating a capacitance signal in response thereto; and
(c) providing an indication in response to said capacitance signal that said particular fluid level in said container has been reached.

37. The method according to claim 36, wherein the detecting step further comprises the steps of:
(b1) measuring the value of said capacitor resulting from changes in the level of said fluid, and generating a capacitance signal in response thereto;
(b2) providing a reference signal indicative of a representative capacitance value corresponding to a particular fluid level; and
(b3) comparing said capacitance signal with said reference signal, and generating an output signal in response to the difference between said capacitance signal and said reference signal.

38. The method according to claim 36, wherein at least portions of said detecting step are performed by a microprocessor.

39. The method according to claim 36, wherein the detecting step further comprises the step of calculating a flow rate of the fluid to or from said container.

40. The method according to claim 39, wherein the indication providing step further comprises the step of providing a visible indication of the calculated flow rate.

41. The method according to claim 36, wherein the detecting step further comprises the step of calculating an estimate of the time in which the fluid will empty from said container.

42. The method according to claim 36, wherein the indication providing step further comprises the step of providing an alarm signal when said particular fluid level in said container has been reached.

43. The method according to claim 36, wherein said member providing step further comprises the step of affixing a portable battery-powered electronic device housing directly to the outside of said apparatus, said housing including two conductive members constructed as an integral part of at least one surface of said housing.

* * * * *